United States Patent
Chatenever et al.

(10) Patent No.: US 6,494,826 B1
(45) Date of Patent: *Dec. 17, 2002

(54) COUPLING FOR A MECHANICAL A LIGHT-GUIDING AND AN IMAGE-GUIDING CONNECTION OF AN ENDOSCOPE TO A CAMERA MODULE

(75) Inventors: David Chatenever, Santa Barbara, CA (US); Klaus M. Irion, Emmingen-Liptingen (DE); André Ehrhardt, Tuttlingen (DE); Jürgen Rudischhauser, Tuttlingen (DE); Daniel Mattsson-Boze, Goleta, CA (US)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/418,542

(22) Filed: Oct. 14, 1999

Related U.S. Application Data

(63) Continuation of application No. PCT/EP98/02078, filed on Apr. 9, 1998.

(30) Foreign Application Priority Data

Apr. 14, 1997 (DE) .......................................... 197 15 510

(51) Int. Cl.[7] ................................................. A61B 1/04
(52) U.S. Cl. ......................... 600/112; 600/117; 600/156
(58) Field of Search ........................ 600/112, 130–132, 600/156, 121, 117, 118

(56) References Cited

U.S. PATENT DOCUMENTS

| | | | | |
|---|---|---|---|---|
| 4,402,313 A | * | 9/1983 | Yabe ........................... | 600/132 |
| 4,754,328 A | * | 6/1988 | Barath et al. ................ | 600/132 |
| 4,807,594 A | * | 2/1989 | Chatenever .................. | 359/513 |
| 4,901,142 A | * | 2/1990 | Ikuno et al. .................. | 348/69 |
| 5,125,394 A | * | 6/1992 | Chatenever et al. ......... | 600/112 |
| 5,193,135 A | * | 3/1993 | Miyagi ........................ | 385/117 |
| 5,311,859 A | * | 5/1994 | Monroe et al. ............... | 348/75 |
| 5,329,936 A | * | 7/1994 | Lafferty et al. .............. | 600/109 |
| 5,591,119 A | * | 1/1997 | Adair .......................... | 600/112 |
| 5,682,199 A | * | 10/1997 | Lankford ...................... | 348/65 |
| 5,879,289 A | * | 3/1999 | Yarush et al. ................ | 600/130 |

\* cited by examiner

*Primary Examiner*—John P. Leubecker
(74) *Attorney, Agent, or Firm*—St. Onge Steward Johnston & Reens LLC

(57) ABSTRACT

A coupling provides mechanical, light-guiding, and image-guiding connection of an endoscope to a camera module. It is proposed that a first cylindrical stem, in whose interior a proximal end segment of the light guiding system is received, project in the coupling direction from a coupling end of the endoscope. Also projecting from the coupling end in the coupling direction is a second approximately cylindrical stem whose length and diameter are greater than the length and diameter of the first stem, a proximal end segment of the image guiding system being received in the interior of the second stem. The second stem coacts with an interlock arranged on the camera module, for mechanical interlocking of the coupling. The first and second stems extend at a distance next to one another, and the coupling end of the camera module has receptacles, complementary to the two stems, into which the two stems penetrate. In the base, the receptacle into which the second stem enters is optically connected to the image sensing system of the camera module, and the receptacle into which the shorter first stem can be received has a light guide.

19 Claims, 3 Drawing Sheets

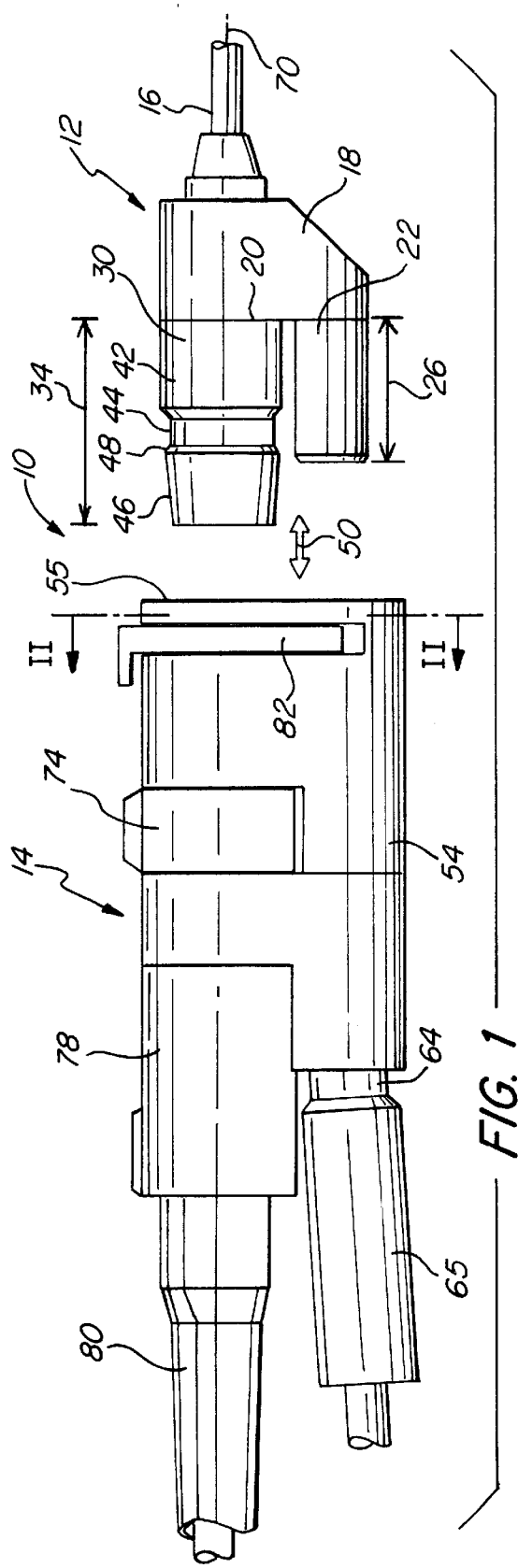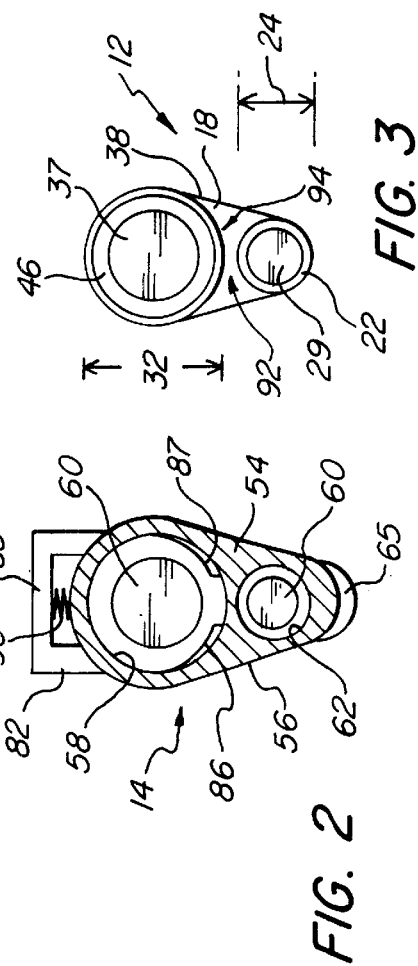
FIG. 1
FIG. 2
FIG. 3

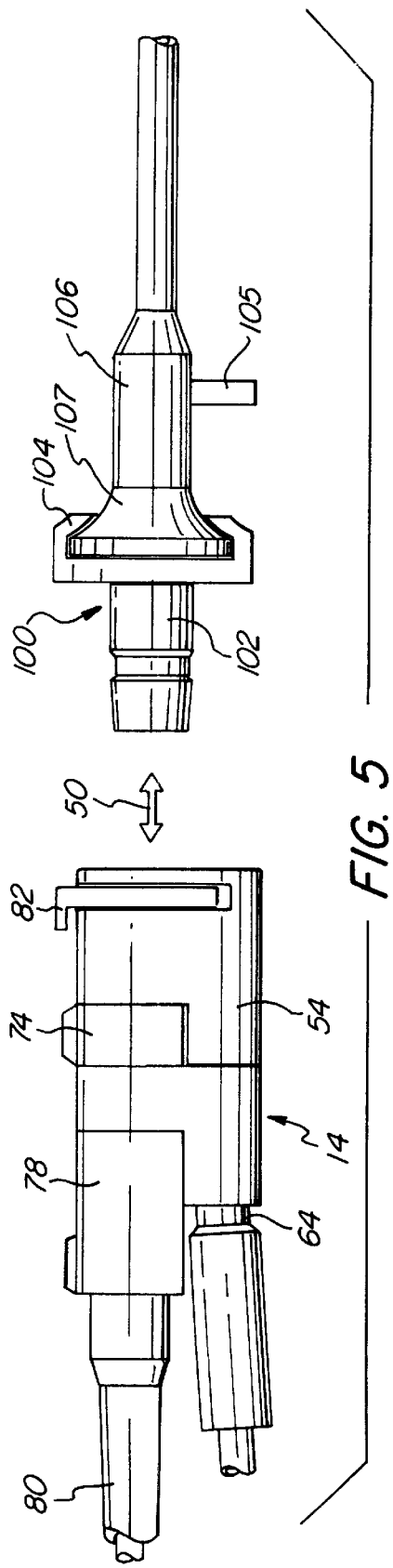
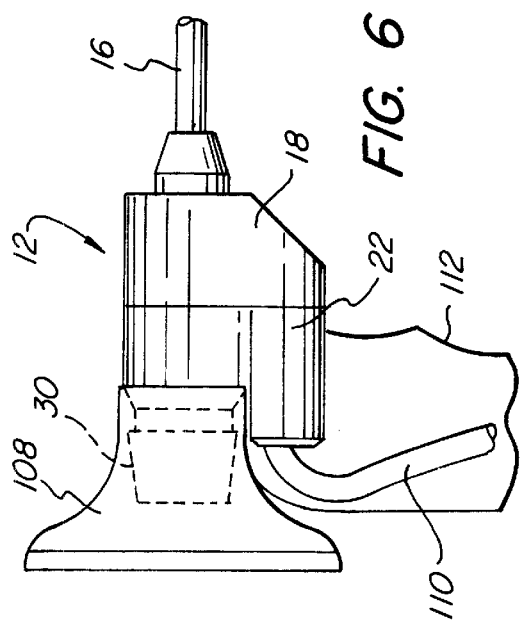

COUPLING FOR A MECHANICAL A LIGHT-GUIDING AND AN IMAGE-GUIDING CONNECTION OF AN ENDOSCOPE TO A CAMERA MODULE

CROSSREFERENCE OF PENDING APPLICATION

This application is a continuation of pending international application PCT/EP98/02078 filed on Apr. 9, 1998.

BACKGROUND OF THE INVENTION

The invention concerns a coupling for a mechanical, a light-guiding, and an image-guiding connection of an endoscope to a camera module, the endoscope having a long cylindrical shaft of approximately constant diameter, the shaft receiving an image guiding system and a light guiding system.

Endoscopes are now widely used in minimally invasive surgery. Endoscopes typically contain an image guiding system, for example in the form of a rod lens system, arranged in the shaft of the endoscope, like the one marketed by the Applicant. The image guiding system can also be configured as an ordered fiber optic bundle. A light guiding system, usually in the form of fiber optic cables, is also present in order to bring light to the surgical area.

At the proximal end, the endoscope or its image guiding system is usually equipped with an eyepiece. The light guiding system usually leads off at right angles from the image guiding system or eyepiece and is connected to a light source via an external light guide.

In a development of this technology, it has become known to equip the proximal end of the endoscope not with an eyepiece but with a camera module that converts the image generated by the endoscope, via an image sensor unit, into a video image that is reproduced, for example, on a monitor. In this case the operator can observe the image generated by the endoscope on a large-screen monitor.

The camera module that is attached at the proximal end of the endoscope usually contains a so-called CCD (charge coupled device) sensor, in the form of a light-sensitive chip that converts the optical signals into electrical signals that are conveyed from the image-sensing camera module to a remotely located image processing system.

To facilitate handling, it has become known to couple the camera. module to an endoscope so that, for example, firstly the endoscope is introduced through a trocar into the surgical area in the body, and the camera module is attached only for the actual operation.

There thus exists a need to couple these two elements in image-guiding fashion. In addition, these elements must also be coupled mechanically to one another so that the attachment does not loosen during the operation or while being handled. At the same time, a light-guiding coupling must be present so that the endoscope or its light guiding system can be connected to a light source.

Not only is a reliable mechanical, light-guiding, and image-guiding connection demanded of such a coupling system, but it should also be possible to perform the coupling procedure with as little close attention as possible, but nevertheless reliably. Provision must therefore be made for the coupling elements of the endoscope on the one hand and of the camera module on the other hand to be coordinated with one another in such a way that they fit into one another and that this is accomplished so that mistakes cannot occur and so that close attention by the operation is not required.

A certain flexibility in terms of other applications is also demanded of such a coupling system.

As mentioned earlier, in many surgical techniques the endoscope is first put into position under direct visual observation, while the camera module is not coupled on. Because an endoscope of this kind possesses no mechanical eyepiece attachment—since this function is of course performed by the camera module—it is difficult for the operator to put the endoscope into position, so that it would be helpful to equip the endoscope briefly with an eyepiece attachment for this procedure.

A variety of approaches have been suggested for creating the mechanical, light-guiding, and image-guiding coupling or connection between endoscope and camera module.

One known approach, in which separate coupling components are provided for each of the three coupling procedures (mechanical, light-guiding, image-guiding), results in a bulky design, for example in the case of the coupling mentioned above having an image guiding system guide that leads off at right angles to the optical axis.

Different coupling directions are present in this case for the individual systems that are to be coupled, so that increased attention is necessary when connecting, and a bulky assemblage results.

It is therefore the object of the present invention to propose a coupling system with which, in a simple, easily handled, and reliable manner, a mechanical, light-guiding, and image-guiding connection can be created between an endoscope and a camera module; this is to be achieved with little design outlay and small dimensions.

SUMMARY OF THE INVENTION

According to the present invention, the object is achieved in that a first cylindrical stem of specific diameter and specific length, in whose interior is received a proximal end segment of the light guiding system, projects from one coupling end of the endoscope in the coupling direction; that there projects from the coupling end of the endoscope, in the coupling direction, a second cylindrical stem whose length and diameter are greater than the length and diameter of the first stem, a proximal end segment of the image guiding system being received in the interior of the second stem, the second stem coacting with an interlock system arranged on the camera module for mechanical coupling, and the first and second stems extending at a distance next to one another; and that complementary receptacles corresponding to the two stems, into which the stems penetrate, are provided at the coupling end of the camera module, a base of the receptacle into which the second stem penetrates being optically connected to the image sensing system of the camera module, and the receptacle in which the shorter first stem is receivable having a light guide.

These features have many considerable advantages in terms of achieving the stated object.

The mechanical, light-guiding, and image-guiding coupling is to be accomplished by way of a single simple linear displacement operation, in which specifically the two stems are pushed into the corresponding receptacles of the camera module. Because the camera module now has a receptacle for a light guide, both the light-guiding connection and the image-guiding connection can be created simultaneously by inserting the components into one another. Because one of the two stems is thicker and longer than the other, incorrect (i.e. reversed) insertion is not possible. Because the thicker stem is also simultaneously the longer one, it is possible, without particular attention, to feel for the correspondingly larger receptacle on the camera module with this thicker and longer stem, and then to close the coupling with an insertion movement. Incorrect attachment is thus no longer possible, since the thicker and longer stem cannot be attached to the smaller-diameter receptacle for the smaller and shorter stem.

The mechanical interlock or coupling is effected simultaneously with this insertion. The fact that this takes place with the larger and thicker stem has the considerable advantage that a stable mechanical join is made to a stable component of the endoscope, namely the long, larger-diameter stem. As a result, the mechanical forces that act on the coupling point can then be absorbed by a very large, stable, and compact component, namely the large and long stem, thus bringing about a coupling with long-term mechanical stability. Because the larger stem is also the longer stem, and it carries the image guiding system, the image-guiding connection occurs at an axial spacing from the light-guiding connection. This feature has the advantage that any stray light that might emerge from the light connection cannot directly come into contact with the image-guiding connecting point located at an axial distance therefrom. The disadvantages of connecting image and light at the same level, or those, for example, of a coaxial arrangement, are thus eliminated.

All that is now present are two compact coupling elements, namely on the one hand the coupling end of the endoscope with the protruding stems arranged parallel to and at a distance from one another, and the camera module with the corresponding receptacles, which also carries the light guide. Because the two stems are arranged next to one another and at a distance, it is still possible to arrange further components in their vicinity without impairing those components. The thicker and longer stem that has penetrated into the camera module and carries the image guiding system of the endoscope comes directly into optical connection, in the base of the receptacle of the camera module, with the optical image sensing system of the camera module; this ensures outstanding optical transmission of the image from the endoscope to the camera module, moreover at a relatively deeply internally located point in the coupling that is therefore protected from external influences, including external light influences. Because the light guide is now also received in the camera module, bulky laterally protruding light guide systems are superfluous.

The object is thus completely achieved by the totality of these features.

In a further embodiment of the invention, the two stems protrude from a housing whose cross-sectional contour corresponds to a contour line running around the two stems of different diameters.

The advantage of this feature is that the tapering oval configuration of the housing can easily be sensed and recognized by the sense of touch of a human hand, so that without visually observing the endoscope, the person handling it knows which of the two stems is located where. In combination with the fact that the thicker stem is in any case longer, it is possible to feel the exact position of the endoscope in the hand without visual contact.

In a further embodiment of the invention, the camera module has in the coupling region a housing whose cross-sectional contour corresponds to a contour line running around the two receptacles of different diameters.

As already mentioned before in conjunction with the configuration of the endoscope, this feature has the advantage that this oval asymmetrical contour can easily be sensed and recognized with the sense of touch of a human hand, so that the exact position of the camera module in the hand can once again be detected without visual observation.

With these two aforementioned configurations in combination, the operator can therefore, for example, sense the endoscope and its precise grasped position in the coupling region with one hand, and with the other hand can easily sense the camera module and its grasped position as well, so that the two elements to be coupled can then be inserted into one another without visual contact. This greatly facilitates handling, especially when, during an operation, one camera module needs to be quickly exchanged for another, or a camera module needs to be coupled to a different endoscope that is also being used during the operation.

In a further embodiment of the invention, the interlock system is configured as a locking element, displaceable transversely to the coupling direction, that can be engaged into a recess on the second stem.

This feature has the advantage that in order to close and/or release the coupling, the locking element is displaced transversely to the coupling direction and engaged into or disengaged from the recess on the second stem. These are all procedures that can be controlled, without visual contact, with the fingers of one hand; the snapping of the locking element into and out of the recess on the stem indicates to the operator whether the coupling is closed or open. If the locking element needs to be pushed into the recess, for example to close the coupling, this can be done by correspondingly actuating the locking element with one finger; precise locking can be ascertained by the fact that the large stem can no longer be moved or pulled out. Conversely, it is also possible to ascertain when, for example, the locking element must be pressed in order to release the coupling. This becomes possible when the large stem comes out of engagement with the locking element and can be pulled off from the camera module. This once again exploits the advantage that the mechanical coupling is accomplished with the relatively large and long stem, which can then also absorb the forces occurring when the coupling is released or is not quite locked.

Numerous embodiments of the locking element are conceivable, for example as ball catches, hooks, snap lugs, or the like.

In a further embodiment of the invention, the locking element is acted upon by the force of a spring, and radially projects slightly into the receptacle for the second stem.

This embodiment has the advantage that on the one hand, the force of the spring presses the locking element into a very defined position, advantageously into the closing position; and because the locking element projects slightly into the receptacle, the thicker stem can only be completely pushed into the receptacle or pulled out from it if the locking element has been moved out. These are all procedures that can be sensed and controlled with the hand's sense of touch, so that no visual attention or observation is necessary when closing and releasing the coupling. This results in a further considerable improvement in ease of handling.

In a further embodiment of the invention, the second stem has on the end a conical segment that is followed by an undercut.

This feature has the advantage that the conical segment constitutes an insertion aid upon insertion of the stem into the receptacle, so that exact insertion is guaranteed with even approximate placement. At the same time,. the conical surface can be utilized to displace the locking element radially upon insertion.

In a further embodiment of the invention, the undercut in the second stem is configured as an annular groove.

This feature has the advantage of making possible a relatively large engagement surface with the locking element, so that the mechanical forces acting on the coupling can be dissipated over a large area, contributing to longevity and mechanical stability.

In a further embodiment of the invention, the locking element protrudes beyond the housing of the camera module.

The advantage of this feature is that the locking element can be easily sensed and actuated, for example, with the fingers of one hand, without requiring a special tool or close attention.

In a further embodiment of the invention, an intermediate imaging system is received in the housing of the endoscope from which the stems protrude.

This feature offers a considerable advantage in terms of standardization of the coupling. Endoscopes of differing shaft diameters are in use, i.e. very thin endoscope shafts in the range of approximately 1 mm up to 10-mm endoscope shafts. Different lens systems with different diameters can accordingly be received in these different endoscopes. If the intermediate imaging system is present in the housing from which the stems protrude, it is then possible, regardless of the diameter of the shaft, to make correspondingly desired images, i.e. images of a specific size or specific image segments, available at the end of the second thicker stem. In other words, one and the same image unit or image unit size can be delivered from the endoscope to the camera module, regardless of whether the endoscope is extremely thick or thin or has different lens diameters. This facilitates handling because the operator then does not need to laboriously set the magnification scale via the image processing system, depending on whether a thin or a thick endoscope is currently attacked to the camera module.

In a further embodiment of the invention, the camera module has an image sensing system with at least one CCD sensor.

This feature, known per se, has the advantage that the camera module can constitute a small, compact component, and the bulky constituents can be located beyond the coupling point.

In a further embodiment of the invention, the camera module has a focusing unit with an adjusting member arranged on the housing.

The advantage of this feature is that a sharp image can be established by way of the focusing unit, directly in the region of the coupling, after coupling has been effected. This is facilitated in particular by the adjusting member arranged on the housing.

In a further embodiment of the invention, the focusing unit effects focusing of the image by shifting lens elements and/or the CCD sensor.

The advantage of this feature is that focusing of the image can be brought about with simple systems, while nevertheless retaining a compact and slender design.

In a further embodiment of the invention, for image erection, the image sensing system is received rotatably in the housing of the camera module.

The term "image erection" is understood to mean a specific horizontal alignment of the monitor image generated by the camera module after the endoscope has been rotated, usually with an asymmetrical direction of view (e.g., 30°), about the shaft axis. Many operators desire a consistent horizontal alignment of the surgical image visible on the monitor when the endoscope is rotated, during an operation, from an initial position. It has become known per se for this purpose correspondingly to rotate the image sensor unit so as thereby to "re-erect" the image.

The feature proposed here—i.e. receiving the rotatable image sensing system in the camera module housing in the region of the coupling—has the considerable advantage in terms of handling that once the coupling has been closed, the image not only can be focused but can also be erected into the desired position, and all these manipulations can be performed with one and the same hand on the coupling.

In a further embodiment of the invention, image erection is accomplished via a rotation capability of the CCD sensor or via an intermediate optical system, e.g. via so-called K prisms.

The advantage of this feature is that image erection can be brought about directly in the camera module housing using elements with compact dimensions.

In a further embodiment of the invention, the second stem and the receptacle receiving it each have a window.

The advantage of this feature is that the image-guiding connection between the image guiding system of the endoscope and the camera can be created by way of mechanically robust and optically transparent means. The window allows sealed closure of the image guiding system of the endoscope so that the latter can be autoclaved without difficulty.

In a further embodiment of the invention, at least one further coupling point for an insufflation duct or flushing duct is provided both in the endoscope and in the camera module.

This feature offers the considerable advantage that with the coupling, it is also simultaneously possible to create a coupling for a flushing duct or insufflation duct present on the endoscope. A corresponding duct is then accordingly provided in the housing of the camera module.

In a further embodiment of the invention, an endoscope-specific coding element, which is coupled to a read element on the camera module, is provided on the housing of the endoscope.

The advantage of this feature is that after the camera module has been coupled, it is possible to detect immediately which endoscope (e.g. direction of view) it has been coupled to, so that specific default image settings in terms of color, filter, image segment, image brightness, hue, or the like can be automatically set, thus also facilitating handling. The coding element can be configured as a mechanical, optical, or electromechanical element.

In a further embodiment of the invention, an adapter is provided that on the one hand is adapted at least to the receptacle of the second stem, and on the other hand can be mounted on a standard endoscope having a standardized eyepiece.

This feature has the considerable advantage that by mounting the adapter, it is possible also to couple a standard endoscope to the camera module. The adapter then has, in any case, the principal orientation feature, namely the large long stem, by way of which the adapter, mounted on the standard endoscope, can be coupled to the camera module. If the standard endoscope has a light guide leading off at right angles, as is usual, the latter can, if applicable, still be led off in that fashion, so that then the capability for the light guide to be received in the camera module no longer needs to be used. This once again shows the considerable advantage of the fact that the large protruding stem is utilized both for mechanical coupling and for image guide coupling, since it is then also possible, by way of the adapter, for a standard endoscope of this kind to be coupled to the camera module.

In a further embodiment of the invention, an eyepiece adapter with light connector can be mounted on the coupling end of the endoscope The considerable advantage of this feature is that by putting the eyepiece adapter in place, it is also possible to look through the endoscope directly with the naked eye. As a result, not only can a corresponding eyepiece be quickly placed onto the endoscope in the event, for example, of a malfunction of the camera system, but this can be done quite deliberately in special cases, for example if the operator, as a result of other activities, wishes to bring his or her eye very close to the endoscope.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be described and explained below in more detail, with reference to several selected exemplary embodiments, in conjunction with the appended drawings, in which:

FIG. 1 shows a side view of the two components to be coupled together, namely the endoscope and camera module, in the uncoupled state;

FIG. 2 shows a section along line II—II in FIG. 1;

FIG. 3 shows a top view of the proximal end of the endoscope;

FIG. 5 shows a variant in which a standard endoscope is to be coupled to a camera module with the aid of an adapter; and FIG. 6 shows an endoscope with an eyepiece adapter attached.

DETAILED DESCRIPTION OF PREFERRED EMBODIMENTS

Figure 4:
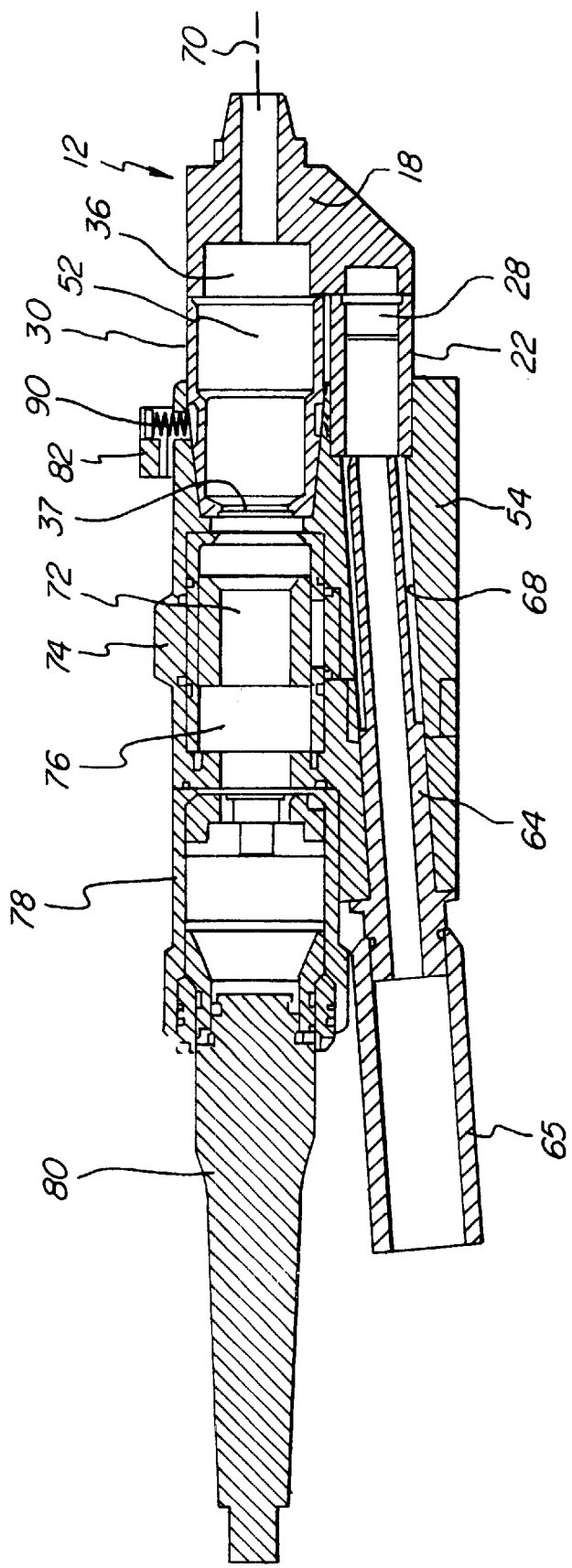
FIG. 4 shows a longitudinal section through the endoscope and camera module of FIG. 1 in a coupled system, the components of the image-guiding and light-guiding system being omitted for the sake of clarity.

A coupling system, labeled in its entirety in FIGS. 1 through 4 with the reference number 10, has an endoscope 12 that is to be coupled to a camera module 14.

Endoscope 12 has an elongated cylindrical shaft 16 that is equipped proximally with a housing 18. A light guiding system and an image guiding system are received, as is general and usual with endoscopes, in shaft 16. An approximately cylindrical first stem 22, which has a diameter 24 and a length 26, protrudes at one coupling end 20 of housing 18.

The proximal end segment of light guiding system 28 (see sectioned representation in FIG. 4) is received in first stem 22. A window 29 forms one proximal termination of stem 22.

Extending from coupling end 20 of housing 18 is a second approximately cylindrical stem 30 that has a diameter 32 and a length 34.

As is evident from the representation in FIG. 2, second stem 30 extends parallel to first stem 22, but at a distance from it. Length 34 of second stem 30 is greater than length 26 of first stem 22. The same applies to diameter 32 of second stem 30.

The purpose of second stem 30 is to receive the proximal end segment of image guiding system 36 of endoscope 12. A window 37 forms one proximal termination of second stem 30.

As is evident in particular from the plan view of FIG. 3, housing 18 has a cross-sectional contour that corresponds to an oval, asymmetrical local line 38 surrounding the two stems 22 and 30. When endoscope 12 is grasped with one hand in the region of housing 18, one thicker and one thinner region is thus perceived.

Second stem 30 has, proceeding from housing 18, a cylindrical segment 42, an annular groove 44, and a terminal conical segment 46. The flank of annular groove 44 inclined toward conical segment 46 simultaneously constitutes an undercut 48. Both stems 22 and 30 extend in a coupling direction 50. The longitudinal center axis of second stem 30 simultaneously constitutes optical axis 70 of the endoscope and of coupling 10.

As is evident in particular from the sectioned representation of FIG. 4, an intermediate imaging system 52 is received in housing 18 and in cylindrical segment 42. This intermediate imaging system 52 serves to bring the image coming from endoscope shaft 16 to a specific identical standardized size at window 37, which is also of a standard size.

Camera module 14 that is to be coupled to endoscope 12 has a housing 54 whose peripheral cross-sectional contour, as is evident in particular from FIG. 2, is delimited by an asymmetrical oval local line 56, i.e. is similar in character to housing 18 of endoscope 12. This again means that when a person's hand grasps housing 54, the impression of one thick and one thin region is conveyed.

Proceeding from one coupling end 55, housing 54 has a first receptacle 58, similar to a blind hole, whose base is closed off by a window 60. The length and inside diameter of receptacle 58 are selected so that second stem 30 can be received snugly therein. Also provided in addition to receptacle 58 is a further receptacle 62 that, as is evident in particular from the sectioned representation of FIG. 4, is configured as a continuous bore 68.

A light guide 64, whose outermost end is closed off with a window 66, is inserted into receptacle 62.

Light guide 64 is inserted into bore 68 sufficiently far that first cylindrical stem 22 can be pushed snugly into receptacle 62, which is approximately similar to a blind hole but is open at the base, as is evident from the sectioned representation of FIG. 4. A nipple 65 of light guide 64, slid onto the end protruding from housing 54, surrounds a fiber optic bundle (not described here in more detail) that is connected to a light source.

As is evident from the sectioned representation of FIG. 4, a focusing unit 72 that has an adjusting ring 74 is provided in housing 54.

An image sensing system 76 is arranged in the optical path behind focusing unit 72. This image sensing system 76 has, for example, a CCD sensor that is usual in this technology, which converts the image from the endoscope, focused by focusing unit 72, into an electrical signal. Image sensing system 76 is received in a sleeve 78 that is received rotatably in a housing 54. Sleeve 78 is equipped at the end with a nipple 80 which surrounds a cable (not described here in more detail) that feeds the electrical signals generated by the CCD sensor to an image processing unit. The rotatability of image sensing systems 76 serves to bring the image on a monitor, coming from endoscope 12, into a specific north-south alignment, i.e. to erect it, if endoscope 12 is rotated.

A locking element 62, displaceable radially to coupling direction 50, is received in housing 54 in the region of coupling end 55.

Locking element 82 has approximately the shape of a two-tined fork whose two tines 86 and 87 are bent inward in a circular shape at the outer end, the radius of curvature corresponding approximately to the radius of curvature of receptacle 58. The two tines 86 and 87 are joined to one another via a clip 88 placed outside the housing. A compression spring 90 that presses locking element 82 radially outward is arranged between clip 88 and housing 54. In this state, the outer ends of tines 86 and 87 project slightly into receptacle 58, as is evident from the sectioned representation of FIG. 2.

For coupling, the two components, i.e. endoscope 12 and camera module 14, are each grasped in one hand, and stems 22 and 30 of endoscope 12 are pushed into the corresponding receptacles 58 and 62.

Conical segment 46 of second stem 30 thereby encounters the ends of tines 86 and 87 projecting into receptacle 58 and displaces them radially outward, moving locking element 82 slightly downward as shown in FIG. 2.

When second stem 30 has been pushed into receptacle 58 to the point that tines 86 and 87 come to rest at the level of annular groove 54, they snap into annular groove 44, assisted by the force of spring 90.

In this position the coupling is now closed, i.e. coupling system 10 is coupled and mechanically interlocked. In this state, window 37 of second stem 30 and window 60 in the base of receptacle 58 lie congruently with one another, thus creating an image-guiding coupling. Window 29 of first stem 22 comes to rest in front of window 60 of light guide 64, so that a light-guiding coupling is also created.

All that is necessary to release the coupling is to press locking element 82 axially inward; as a result, the curved ends of tines 86 and 87 come out of annular groove 44, so that endoscope 12 can be pulled off camera module 14.

It is evident from the plan view of FIG. 3 that a further coupling point 92 can be provided in housing 18 of the endoscope and then also, correspondingly, in housing 54 of the camera module, for example in the form of an insufflation duct or flushing duct.

It is also possible to provide on housing 18 of endoscope 12 a coding element 94 that can be read by camera module 14, making it possible to recognize which endoscope 12 has been coupled to it.

FIG. 5 shows a further embodiment of the coupling system; camera module 14 shown on the left-hand side corresponds exactly to the camera module shown in FIG. 1.

In this case, a standard endoscope having a standard eyepiece and a lateral light connector 105 is to be coupled to camera module 14. This is done by attaching onto eyepiece 107 an adapter 100 from which there projects a stem 102 that corresponds in contour, size, length, and diameter to second stem 30. Adapter 100 is secured on eyepiece 107 of standard endoscope 106 by way of a claw coupling 104.

This assemblage can now be coupled to camera module 14 once again in coupling direction 50 as described earlier. Since light guide connector 105 proceeds off at a right angle in this case, light guide 64 does not need to be utilized. It is also possible, however, to provide on adapter 100 a stem corresponding to first stem 22, which can then be connected to the light connector 105, leading off laterally, of standard endoscope 106.

FIG. 6 shows how the capability of observing visually through endoscope 12 is created on endoscope 12 by way of an eyepiece adapter 108. For this purpose, eyepiece adapter 108 is slid onto second stem 30 of endoscope 12. A handle 112 contains a light connector 110 that leads the light guide off laterally out of first stem 22. It is thus possible to observe visually through endoscope 12, unimpeded by the light guide.

What is claimed is:

1. A coupling for a mechanical, a light-guiding, and an image-guiding connection of an endoscope to a camera module, said camera module is provided with an interlock system for mechanical interlocking said coupling, said coupling comprising as a first coupling element a coupling end on said endoscope and as a second coupling element a coupling end on said camera module, said endoscope having a long cylindrical shaft of approximately constant diameter, said shaft receiving an image guiding system and a light guiding system, comprising:
a first cylindrical stem projecting from said coupling end of said endoscope in a direction of movement of said two coupling elements during closing or opening of said coupling, said first cylindrical stem has a first diameter and a first length, in an interior of said first cylindrical stem a proximal end section of said light guiding system is received, and
a second approximately cylindrical stem projecting from said coupling end of said endoscope in said coupling direction, said second stem has a second length and a second diameter greater than the first length and the first diameter of said first stem, in an interior of said second stem a proximal end section of said image guiding system is received, said second stem coacting with said interlock system of said camera module for mechanical interlocking of said coupling, with said first stem and said second stem extending at a distance next to one another,
wherein said coupling end of said camera module is provided with a first and a second receptacle corresponding to said two stems, into which receptacle penetrates the corresponding stem when closing said coupling, said first receptacle for receiving said shorter first stem is provided with a light guide, and wherein said second receptacle for receiving said second stem is provided with a base optically connected to an image sensing system of said camera module; and
wherein said interlock system is configured as a locking element, displaceable transversely to said direction of movement of said two coupling elements during closing or opening of said coupling, and said locking element can engage into a recess provided on said second stem.

2. The coupling of claim 1, wherein the locking element is acted upon by force of a spring, and the locking element is radially pushed by said spring into the second receptacle for said second stem.

3. The coupling of claim 2, wherein the second stem has a conical end section followed by an undercut.

4. The coupling of claim 3, wherein said undercut is configured as an annular groove of said second stem.

5. The coupling of claim 4, wherein the locking element protrudes beyond a housing of said camera.

6. The coupling of claim 1, wherein an intermediate image system is received in a housing of said endoscope, from which housing said two stems protrude.

7. The coupling of claim 1, wherein said camera module comprises an image sensing system with at least one CCD sensor.

8. The coupling of claim 7, wherein for image erection, said image sensing system is received rotatably in said camera module.

9. The coupling of claim 8, wherein said image erection is accomplished by means selected from the group comprising: a rotation capability of a CCD sensor, an intermediate optical system, or K prisms.

10. The coupling of claim 1, wherein said camera module is provided with a focusing unit having an adjusting member arranged on said housing.

11. The coupling of claim 10, wherein said focusing unit effects focusing of an image by elements selected from the group consisting of shifting lens elements and a CCD sensor.

12. The coupling of claim 1, wherein the second stem and said second receptacle receiving it each have a window.

13. The coupling of claim 1, wherein at least one further coupling point for coupling to an insufflation duct is provided both in said endoscope and in said camera.

14. The coupling of claim 1, wherein at least one further coupling point for coupling to a flushing duct is provided both in said endoscope and in said camera.

15. The coupling of claim 1, wherein an endoscope-specific coding element that is coupled to a read element on said camera module is provided on a housing of said endoscope.

16. The coupling of claim 1, wherein an adapter is provided that is adapted for receiving the second receptacle, for receiving the second stem, and is adapted for use with a standard endoscope having a standardized eyepiece.

17. The coupling of claim 1, wherein an eyepiece adapter with a light connector is mounted on a coupling end of said endoscope.

18. A coupling for connecting an endoscope to a camera, where the camera is provided with an interlock system for mechanical interlocking of the coupling, and with a first and a second receptacle that comprise a camera coupling element, the coupling comprising:

an endoscope, having a long cylindrical shaft of approximately constant diameter, said shaft receiving an image guiding system and a light guiding system, the shaft including:

a first cylindrical stem projecting from a coupling end of the endoscope in a direction of movement of the endoscope and camera during closing or opening of the coupling, the first cylindrical stem having a first diameter and a first length, and in an interior of the first cylindrical stem a proximal end section of the light guiding system is received, and a second approximately cylindrical stem projecting from a coupling end of said endoscope in a coupling direction, said second stem having a second length and a second diameter greater than the first length and the first diameter of said first stem, and in an interior of said second stem a proximal end section of the image guiding system is received, said second stem being designed to coact with an interlock system of a camera for mechanical interlocking of the coupling, with said first stem and said second stem extending at a distance next to one another, and wherein the two stems comprise an endoscope coupling element that is designed to be received within the camera coupling element, and the interlock system is configured as a locking element, displaceable transversely to the direction of movement of the two coupling elements during closing or opening of said coupling, and said locking element can engage into a recess provided on said second stem.

19. A coupling for connecting an endoscope to a camera, where the endoscope is provided with an endoscope coupling element including a first cylindrical stem, for a light guiding system, with a first diameter and a first length, and a second cylindrical stem, for an image guiding system, with a second diameter and a second length, the second length and second diameter being greater than the first length and the first diameter of the first stem, the coupling comprising:

a camera, having a coupling element including a first and a second receptacle, designed to receive the endoscope coupling element, said first receptacle designed for receiving a first stem is provided with a light guide, and the second receptacle designed for receiving a second stem is provided with a base optically connected to an image sensing system of said camera;

wherein an interlock system configured as a locking element, displaceable transversely to a direction of movement of the two coupling elements during closing or opening of the coupling, and the locking element can engage into a recess provided on the second stem.

* * * * *

UNITED STATES PATENT AND TRADEMARK OFFICE
CERTIFICATE OF CORRECTION

PATENT NO.     : 6,494,826 B1
DATED          : December 17, 2002
INVENTOR(S)    : David Chatenever et al.

It is certified that error appears in the above-identified patent and that said Letters Patent is hereby corrected as shown below:

<u>Title page,</u>
Item [54], should read -- [54] COUPLING FOR A MECHANICAL, A LIGHT-GUIDING AND AN IMAGE-GUIDING CONNECTION OF AN ENDOSCOPE TO A CAMERA MODULE --

Signed and Sealed this

Fifteenth Day of April, 2003

JAMES E. ROGAN
*Director of the United States Patent and Trademark Office*